United States Patent
Kirschner et al.

(10) Patent No.: US 6,899,890 B2
(45) Date of Patent: May 31, 2005

(54) BIOADHESIVE DRUG DELIVERY SYSTEM

(75) Inventors: Mitchell I. Kirschner, St. Louis, MO (US); R. Saul Levinson, Chesterfield, MO (US); Thomas C. Riley, Manchester, MO (US); Marc S. Hermelin, St. Louis, MO (US)

(73) Assignee: KV Pharmaceutical Company, St. Louis, MO (US)

( * ) Notice: Subject to any disclaimer, the term of this patent is extended or adjusted under 35 U.S.C. 154(b) by 403 days.

(21) Appl. No.: 10/101,014

(22) Filed: Mar. 20, 2002

(65) Prior Publication Data

US 2003/0180366 A1 Sep. 25, 2003

(51) Int. Cl.⁷ .......................... A61F 13/02; A61F 6/06; A61F 6/14; A61K 9/107; A61N 25/34
(52) U.S. Cl. .................. 424/430; 424/434; 424/431; 424/432; 424/433; 424/401; 424/404
(58) Field of Search ................ 424/430, 434, 424/431, 432, 433, 401, 404

(56) References Cited

U.S. PATENT DOCUMENTS

| | | | |
|---|---|---|---|
| 3,988,508 A | 10/1976 | Lissant | 526/344.2 |
| 4,551,148 A | 11/1985 | Riley, Jr. et al. | 424/430 |
| 4,895,452 A | 1/1990 | Yiournas et al. | 366/165.1 |
| 5,055,303 A | 10/1991 | Riley, Jr. | 424/436 |
| 5,189,070 A | 2/1993 | Brownscombe et al. | 521/64 |
| 5,266,329 A | 11/1993 | Riley, Jr. | 424/430 |
| 5,298,246 A | 3/1994 | Yano et al. | 424/94.1 |
| 5,536,743 A * | 7/1996 | Borgman | 514/398 |
| 5,622,657 A | 4/1997 | Takada | 264/4.32 |
| 5,716,637 A | 2/1998 | Anselem et al. | |
| 5,733,939 A | 3/1998 | Fuhrman et al. | 514/759 |
| 5,814,330 A | 9/1998 | Putteman et al. | |
| 5,840,744 A | 11/1998 | Borgman | 514/398 |
| 5,877,216 A | 3/1999 | Place et al. | 514/573 |
| 5,980,936 A | 11/1999 | Krafft et al. | 424/450 |
| 5,993,846 A | 11/1999 | Friedman et al. | 424/434 |
| 6,191,105 B1 | 2/2001 | Ekwuribe et al. | 514/3 |
| 6,294,550 B1 | 9/2001 | Place et al. | 514/302 |

FOREIGN PATENT DOCUMENTS

EP 0 404 376 12/1990

* cited by examiner

*Primary Examiner*—Carlos A. Azpuru
(74) *Attorney, Agent, or Firm*—Gary M. Nath

(57) ABSTRACT

The present invention relates to a novel essentially pH neutral vaginal drug delivery system suitable for modified delivery of a therapeutically active material in the vaginal cavity. The vaginal drug delivery system comprises an essentially pH neutral emulsion having globules having two phases, an internal water soluble phase and an external water-insoluble phase or film, wherein the water-soluble interior phase contains a therapeutically active drug or drugs. One novel aspect of the vaginal drug delivery system is that the internal water soluble phase comprises an acidic buffered phase.

57 Claims, No Drawings

BIOADHESIVE DRUG DELIVERY SYSTEM

BACKGROUND OF THE INVENTION

1. Field of the Invention

The present invention relates to a novel essentially pH neutral vaginal drug delivery system suitable for modified delivery of a therapeutically active material in the vaginal cavity which optimizes the chances for cure associated with the therapeutically active material. The vaginal drug delivery system comprises an essentially pH neutral emulsion having globules having two phases, an internal water soluble phase and an external water-insoluble phase or film, wherein the water-soluble interior phase contains a therapeutically active drug or drugs. One novel aspect of the vaginal drug delivery system is that the internal water soluble phase comprises an acidic buffered phase which is isotonic, hypertonic, or hypotonic. The present invention further relates to a method of treating a vaginal disorder using these drug delivery systems.

2. Description of the Related Art

One of the main disciplines of medicine is the management of the female reproductive system for the diagnosis, prevention, mitigation, treatment, and cure of diseases, as well as the prevention or enhancement of conception. Usually, this involves the direct delivery of active agents to the vaginal cavity and its environs.

Because the vaginal cavity is subject to conditions which render it a target for disease and infection, systems to effect the delivery of such agents are usually in the form of gels, foams, creams, suppositories, and quick dissolving tablets. These delivery systems, regardless of formulation or method of manufacture, have demonstrated some difficulty in their ability to deliver active agents in a controlled manner within the vaginal cavity for periods of three hours or longer. It is extremely difficult to deliver an active agent to this area for an extended period of time.

The vaginal cavity exhibits an aqueous environment containing secreting glands whose fluids create an acidic pH in the range of 4.5 to 5.5. The environment of the vagina is conducive to the growth of bacteria, fungi, yeast, and other microorganisms since it is warm, moist, and dark. Further, the physical structure is a vestibule for menstrual debris and residual seminal fluid from sexual intercourse, undesirable bacteria, fungi, yeast, and other microorganisms. The vaginal cavity is also subject to considerable physical deformation, such as during sexual intercourse or during the insertion of tampons.

Active agents which have pharmaceutical qualities have been developed and approved for use in the treatment of afflictions of the vaginal cavity and the prevention of conception. These active agents include fungicides, spermicides, etc. However, it has been difficult to achieve optimal potential effectiveness of these agents due to the inadequacy of known delivery systems. Systems which are presently approved or even suitable for use in the vaginal cavity have shown some difficulty in the release of a pharmaceutically active agent(s) for an extended period of time. This also is true of aesthetically oriented systems, such as acidifiers and deodorants.

The vast majority of gels, foams, creams, suppositories, and tablets that are presently used as vaginal delivery systems breakdown almost immediately following insertion into the vaginal cavity and have minimal bioadherence to the vaginal walls. This is believed to be due to their water miscibility and/or their lack of physical stability at 37° C. (body temperature). Thus, they exhibit limited effectiveness due to rapid, uncontrolled release of the active agents. Additionally, conventional dosage forms frequently discharge a leakage and drippage. To minimize this rapid leakage, most conventional dosage forms are administered at night just before the patient goes to sleep in a prone position.

A modified release system delivers the active agent to the sites of action, absorption, or use in a predetermined manner. This contrasts with conventional immediate release systems which require frequent repetitive dosing in order to achieve the desired level of active agent. An advantage of a modified release system is that the drug is administered fewer times a day than conventional systems since the drug level in the vaginal cavity is maintained at a constant rate. Additionally, the controlled release systems of the prior art do not affect the total number of days that are required to treat a condition.

Emulsions can be useful for the preparation of a modified release drug delivery system. Emulsions generally possess a high free energy protective barrier. In particular, emulsions having a relatively high ratio of water to oil and possessing high free energy are known in the art as High Internal Phase Emulsions ("HIPE's"). HIPE's have been used in various applications such as fuels, agricultural sprays, textile printing, foods, household and industrial cleaning, cosmetics and drugs, and fire extinguishers. HIPE's have also been used in producing polymeric foam-type materials. See, for example, U.S. Pat. No. 3,988,508 ("Lissant"); and U.S. Pat. No. 5,189,070 ("Brownscombe et al."), each of which is hereby incorporated by reference in its entirety.

The most significant feature of known HIPEs is that the emulsions typically break down in the gastrointestinal and/or digestive tracts and lose internal phase energy, which causes the emulsion to coalesce into a continuous film on the mucosal membrane.

Several controlled release emulsions for use in the delivery of pharmaceuticals are known in the art. For example, U.S. Pat. No. 5,298,246 ("Yano et al."), hereby incorporated by reference in its entirety, discloses oil-in-water emulsions for improving the absorbability of lipophilic drugs through oral administration. The emulsions are kept stable by adding a sodium phosphate isotonic buffer (pH 7.0).

U.S. Pat. No. 5,622,657 ("Takada et al."), hereby incorporated by reference in its entirety, discloses a process for producing microparticle preparations having a prolonged release. These preparations can include a water-in-oil type emulsion and can be administered vaginally.

U.S. Pat. No. 5,733,939 ("Fuhrman et al."), hereby incorporated by reference in its entirety, discloses a conventional drug delivery form for the treatment of mucosal inflammation, including the vaginal mucosa. This reference contemplates emulsions with a continuous gaseous or liquid fluorocarbon phase and a discontinuous aqueous phase in the form of gels.

U.S. Pat. No. 5,840,744 ("Borgman"), hereby incorporated by reference in its entirety, discloses a non-flowing metronidazole composition for the treatment of bacterial vaginosis. The disclosed metronidazole compositions can be buffered to an acidic pH. This reference contemplates water-in-oil emulsions wherein the metronidazole and buffer salts are dissolved or suspended in the oil phase ingredients.

U.S. Pat. No. 5,993,846 ("Friedman et al."), hereby incorporated by reference in its entirety, discloses an emulsion for application to a mucosal surface, such as the vaginal mucosa. In particular, Friedman discloses lipid-in-water type emulsions containing drugs with enhanced bioadhesive properties.

U.S. Pat. No. 6,191,105 ("Ekwuribe et al."), hereby incorporated by reference in its entirety, discloses microemulsion formulations of free-form and/or conjugation-stabilized therapeutic agents. The microemulsion comprises a water-in-oil emulsion. Ekwuribe discloses that the pH of the emulsions as a whole can be adjusted for compatibility with the nasal mucus membranes and eyes to which they are administered. Ekwuribe also contemplates vaginal administration of the disclosed formulations.

U.S. Pat. No. 6,294,550 ("Place et al."), hereby incorporated by reference in its entirety, discloses a conventional drug delivery form for the treatment of female sexual dysfunction. This reference contemplates water-on-oil emulsions for vaginal delivery.

Nevertheless, broad spectrum use of the drug delivery systems described herein is precluded either because: (1) the known systems require toxic amounts of adjuvants or inhibitors; (2) suitable low molecular weight therapeutics are not available; (3) the known systems exhibit poor stability and inadequate shelf life; (4) the known systems are difficult to manufacture; (5) the known systems fail to protect the active agent; (6) the known systems adversely alter the active agent; (7) the known systems fail to allow or promote absorption of the active agent; and/or (8) the known systems fail to deliver the active agent over a sufficiently extensive period of time.

Accordingly, an aspect of the presently claimed invention is to provide an essentially pH neutral vaginal drug delivery system comprising an essentially pH neutral emulsion having globules having two phases, an internal, acidic buffered water-soluble phase containing a therapeutically active drug or drugs and an external water-insoluble phase or film. This drug delivery system is advantageous in that it provides for the delivery of a therapeutically active drug or drugs in a modified manner in the vaginal cavity for an extended period of up to 168 hours. Accordingly, the drug delivery system optimizes the drug delivery efficacy, the therapeutic effects of the drug or drugs, and the chances for cure provided by the therapeutically active drug or drugs. The system may take the form of a multi-phase liquid or semi-solid which is easily introduced into the vaginal cavity but does not actively seep from this body cavity. It is further advantageous since it reduces the treatment period for active agents.

These and other aspects of the invention will be apparent from the detailed description and the claims.

SUMMARY OF THE INVENTION

The present inventive subject matter relates to an essentially pH neutral vaginal drug delivery system comprised of an essentially pH neutral emulsion having globules having two phases, and methods of manufacturing and using the vaginal drug delivery system.

More particularly, the present inventive subject matter relates to an essentially pH neutral vaginal drug delivery system, which comprises:
an essentially pH neutral emulsion having globules having two phases, an internal water-soluble phase and an external water-insoluble phase or film;
said internal water-soluble phase comprises an acidic buffered phase containing a therapeutically active drug or drugs, wherein the acidic buffered phase comprises said therapeutically active drug or drugs either alone or in combination with an additional buffering agent;
wherein the acidic buffered phase is isotonic, hypertonic, or hypotonic.

Another embodiment of the present inventive subject matter is an essentially pH neutral vaginal drug delivery system, which comprises:
an essentially pH neutral emulsion having globules having two phases, an internal water-soluble phase and an external water-insoluble phase or film;
said internal water-soluble phase comprises an acidic buffered phase containing a micronized therapeutically active drug or drugs, wherein the acidic buffered phase comprises said micronized therapeutically active drug or drugs either alone or in combination with an additional buffering agent;
wherein the acidic buffered phase is isotonic, hypertonic, or hypotonic; and
wherein the micronized therapeutically active drug has a particle size ranging from about 0.1 microns to less than 60.0 microns;
wherein the efficacy of the therapeutically active drug is maximized by the acidic buffered phase; and
wherein the acidic buffered phase is present in an amount sufficient to provide a cessation of symptoms of irritation and itching of the vaginal mucosa.

Yet another embodiment of the present inventive subject matter is an essentially pH neutral vaginal drug delivery system, which comprises:
an essentially pH neutral emulsion having globules having two phases, an internal water-soluble phase and an external water-insoluble phase or film;
said internal water-soluble phase comprises an acidic buffered phase having an internal pH of about 2.0 to about 6.0 and a therapeutically active drug, wherein the acidic buffered phase comprises said therapeutically active drug either alone or in combination with an additional buffering agent.

Another embodiment of the present inventive subject matter is a method for treating a vaginal disorder comprising: administering to a patient an essentially pH neutral vaginal drug delivery system, which comprises:
an essentially pH neutral emulsion having globules having two phases, an internal water-soluble phase and an external water-insoluble phase or film;
said internal water-soluble phase comprises an acidic buffered phase containing a therapeutically active drug or drugs, wherein the acidic buffered phase comprises said therapeutically active drug or drugs either alone or in combination with an additional buffering agent;
wherein the acidic buffered phase is isotonic, hypertonic, or hypotonic; and
wherein the therapeutically active drug has a particle size ranging from about 0.1 microns to less than 60.0 microns.

DETAILED DESCRIPTION OF THE INVENTION

As used herein to describe an emulsion having globules, the term "globule" indicate globules having a rounded shape produced by high shear homogenization. Additionally, the globules as described herein have two phases, an internal water-soluble phase comprising an acidic buffered phase and an external water-insoluble phase or film.

The drug delivery systems according to the presently claimed invention are "essentially pH neutral", that is substantially pH neutral as a whole in that the pH of these drug delivery systems is not measurable due to the discontinuous aqueous phase. Hence, these drug delivery systems do not exhibit a pH when intact. Only the buffered internal phase of the globules making up the instant drug delivery system has a non-neutral (acidic) measurable pH.

As used herein with regard to globules, the term "average diameter" is the value obtained using a particle size analyzer, such as for example, the SediGraph 5100, which is commercially available from Micromeritics (Norcross, Ga.). Alternatively, average diameter can be determined by measuring the diameters of at least 100 globules in a photograph (s) taken using an optical microscope.

The term "oil" is used herein with regard to the continuous phase of the emulsion, a component of the interphase, or the suspension medium described herein to indicate that these media are hydrophobic and therefore immiscible with the hydrophilic phase. This term does not imply that these phases must consist of or include oils.

The terms "stable" or "stabilized", as used herein, mean that the globules formed thereby are substantially resistant to unwanted degradation, either in storage or upon administration to the vaginal cavity.

The term "biocompatible" means a lipid or polymer which, when introduced into the tissues of a human patient, either alone or in combination with a pH control, will not result in any degree of unacceptable toxicity, including allergenic responses and disease states. Preferably the lipids or polymers are inert.

The term "micronized" as used herein refers to a particle size range of about 0.1 microns to less than 60 microns. Micronized therapeutically active drug or drugs improve the efficacy of vaginal delivery systems since they approach the optimum size of the globule carriers that engulf the micronized particles.

The present inventive subject matter is directed to vaginal delivery systems. The systems are characterized by their ability to deliver therapeutically active drug or drugs to a specific site, the vaginal cavity, in a modified manner over a prolonged period of time, maximizing the therapeutic effects of the drug or drugs, as well as the drug delivery efficacy. The systems are bioadherent to the epithelial tissue and are comprised of at least two phases. The systems retain their integrity and display physical stability for an extended residence time within the vaginal cavity.

As discussed above, the vaginal cavity produces an aqueous environment which is conducive to the growth of bacteria, fungi, yeast, and microorganisms. The systems of the prior art are not optimally effective for treating such conditions either due to their water miscibility, lack of bioadhesion, or lack of physical stability in the vaginal environment of 37° C. The "vaginal cavity" as defined herein not only includes the vagina, but also any additional contiguous tissues or surfaces. These contiguous tissues or surfaces include any part of the female urogenital tract, such as the ostium of the urethra, cervix, uterus, vulva, fallopian tubes, bladder, colon, anus, rectum, ovaries, ureter, and uterine tubes. "Delivery systems" are a combination of non-active ingredients which serve to solubilize, suspend, thicken, dilute, emulsify, stabilize, preserve, protect, color, flavor, and fashion a therapeutically active drug or drugs into an acceptable and efficacious preparation for the safe and convenient delivery of an accurate dose of said therapeutically active drug or drugs.

The present inventive vaginal drug delivery systems are suitable for modified delivery of a therapeutically active drug or drugs to the vaginal cavity. These vaginal drug delivery systems comprise an essentially pH neutral emulsion having globules defining an external water-insoluble phase or film and an internal water-soluble phase, wherein the internal water-soluble phase comprises an acidic buffered phase containing a therapeutically active drug or drugs, wherein the acidic buffered phase comprises said therapeutically active drug or drugs either alone or in combination with an additional buffering agent.

Typically, the globules used in this invention have a diameter from about 0.1 microns to about 100 microns. In a preferred embodiment, the globules have a particle size ranging from about 0.1 microns to about 60 microns. In a particularly preferred embodiment, the globules have a particle size ranging from about 0.5 microns to about 55 microns.

The exterior of the globules of the present invention are constructed from biocompatible lipid or polymer materials, and of these, the biocompatible lipids are especially preferred. For the biocompatible lipid materials, amphiphilic or hydrophobic compositions are preferred. Amphiphilic compositions refer to any composition of matter which has both lipophilic (hydrophobic) and hydrophilic properties.

Natural and synthetic phospholipids are examples of lipids useful as emulsifiers in preparing the exterior of the globules used in the present invention. They contain charged phosphate "head" groups, which are hydrophilic, attached to long hydrocarbon tails, which are hydrophobic. This structure allows the phospholipids to achieve a single bilayer (unilamellar) arrangement in which all of the water-insoluble hydrocarbon tails are in contact with one another, leaving the highly charged phosphate head regions free to interact with a polar aqueous environment. It will be appreciated that a series of concentric bilayers are possible, i.e., oligolamellar and multilamellar, and such arrangements are also contemplated to be within the scope of the presently claimed invention. In particular, phospholipids and phospholipid esters increase the stability of the present emulsions. This is of particular importance where aggressive therapeutically active drugs are used.

The most useful stabilizing compounds for preparing the walls of the present globules are typically those which have a hydrophobic/hydrophilic character allowing them to form bilayers in the presence of a water based medium. Thus, water, saline, or some other water based medium, often referred to hereafter as a diluent, may be an aspect of the globules of the present invention where such bilayer forming compositions are used as the stabilizing compounds.

Preferred amphiphilic or hydrophobic materials of use according to the presently claimed invention are selected from the group consisting of mineral oil, lipid material, neutral fats, fatty acids, fatty acid esters, vegetable oils, vitamin oils, fruit oils, fish oils, any other oils derived from plants or animals, and mixtures and combinations thereof. A particularly preferred lipid according to the present inventive subject matter is a phospholipid.

The stability of the resultant globules of the present invention may be attributable to the non-Newtonian physical properties demonstrated by globules obtained by a high shear homogenization process. Other notable features of a high shear homogenization process are a high free surface energy and an affinity between globules.

It is not necessary to employ auxiliary stabilizing additives to the globules produced according to the present inventive subject matter, although it is optional to do so, and such auxiliary stabilizing agents would be within the knowledge of one ordinarily skilled in the art.

The biocompatible polymers useful as stabilizing compounds for preparing the globules used in the presently claimed invention can be of either natural, semi-synthetic, or synthetic origin.

As used herein, the term polymer denotes a compound comprised of two or more repeating monomeric units, and preferably 10 or more repeating monomeric units.

The term semi-synthetic polymer, as employed herein, denotes a natural polymer that has been chemically modified in some fashion. Exemplary natural polymers suitable for use in the present invention include naturally occurring polysaccharides. Such polysaccharides include, for example, arabinans, fructans, fucans, galactans, galacturonans, glucans, mannans, xylans (such as, for example, inulin), levan, fucoidan, carrageenan, galatocarolose, pectic acid, pectin, amylose, pullulan, glycogen, amylopectin, cellulose, dextran, pustulan, chitin, agarose, keratan, chondroitan, dermatan, hyaluronic acid, alginic acid, xanthan gum, starch, and various other natural homopolymer or heteropolymers such as those containing one or more of the following aldoses, ketoses, acids, or amines: erythrose, threose, ribose, arabinose, xylose, lyxose, allose, altrose, glucose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, neuraminic acid, and naturally occurring derivatives thereof.

Exemplary semi-synthetic polymers suitable for use according to the presently claimed invention include carboxymethylcellulose, hydroxymethylcellulose, hydroxypropylmethylcellulose, methylcellulose, and methoxycellulose.

Exemplary synthetic polymers suitable for use according to the present invention include polyethylenes (such as, for example, polyethylene glycol, polyoxyethylene, and polyethylene terephthlate), polypropylenes (such as, for example, polypropylene glycol), polyurethanes (such as, for example, polyvinyl alcohol (PVA), polyvinylchloride, and polyvinylpyrrolidone), polyamides including nylon, polystyrene, polylactic acids, fluorinated hydrocarbons, fluorinated carbons (such as, for example, polytetrafluoroethylene), polymethylmethacrylate, and derivatives thereof.

Additional lipids or oils which may be used to prepare the exterior phase or film of the globules used in the present invention include but are not limited to: fatty acids, lysolipids, phosphatidylcholine with both saturated and unsaturated lipids including dioleoylphosphatidylcholine; dimyristoylphosphatidylcholine; dipentadecanoylphosphatidylcholine; dilauroylphosphatidylcholine; dipalmitoylphosphatidylcholine (DPPC); distearoylphosphatidylcholine (DSPC); phosphatidylethanolamines such as dioleoylphosphatidylethanolamine and dipalmitoylphosphatidylethanolamine (DPPE); phosphatidylserine; phosphatidylglycerol; phosphatidylinositol; sphingolipids such as sphingomyelin; glycolipids such as ganglioside GM1 and GM2; glucolipids; sulfatides; glycosphingolipids; phosphatidic acids such as dipalymitoylphosphatidic acid (DPPA); DHA; omega-3 oil; omega-6 oil; canola oil; citrus oil; hydrogenate vegetable oil; mineral oil; corn oil; cottonseed oil; peanut oil; sesame oil; soybean oil; palmitic acid; stearic acid; arachidonic acid; oleic acid; lipids bearing polymers such as polyethyleneglycol, i.e., PEGylated lipids, chitin, hyaluronic acid, or polyvinylpyrrolidone; lipids bearing sulfonated mono-, di-, oligo-, or polysaccharides; cholesterol, cholesterol sulfate, and cholesterol hemisuccinate; tocopherol hemisuccinate; lipids with ether and ester-linked fatty acids; polymerized lipids (a wide variety of which are well known in the art); diacetyl phosphate; dicetyl phosphate; stearylamine; cardiolipin; phospholipids with short chain fatty acids of 6–8 carbons in length; synthetic phospholipids with asymmetric acyl chains (e.g., with one acyl chain of 6 carbons and another acyl chain of 12 carbons); ceramides; non-ionic liposomes including niosomes such as polyoxyethylene fatty acid esters, polyoxyethylene fatty alcohols, polyoxyethylene fatty alcohol ethers, polyoxyethylated sorbitan fatty acid esters, glycerol polyethylene glycol oxystearate, glycerol polyethylene glycol ricinoleate, ethoxylated soybean sterols, ethoxylated castor oil, polyoxyethylene-polyoxypropylene polymers, and polyoxyethylene fatty acid stearates; sterol aliphatic acid esters including cholesterol sulfate, cholesterol butyrate, cholesterol iso-butyrate, cholesterol palmitate, cholesterol stearate, lanosterol acetate, ergosterol palmitate, and phytosterol n-butyrate; sterol esters of sugar acids including cholesterol glucuronide, lanosterol glucuronide, 7-dehydrocholesterol glucuronide, ergosterol glucuronide, cholesterol gluconate, lanosterol gluconate, and ergosterol gluconate; esters of sugar acids and alcohols including lauryl glucuronide, stearoyl glucuronide, myristoyl glucuronide, lauryl gluconate, myristoyl gluconate, and stearoyl gluconate; esters of sugars and aliphatic acids including sucrose laurate, fructose laurate, sucrose palmitate, sucrose stearate, glucuronic acid, gluconic acid, accharic acid, and polyuronic acid; saponins including sarsasapogenin, smilagenin, hederagenin, oleanolic acid, and digitoxigenin; glycerol dilaurate, glycerol trilaurate, glycerol dipalmitate, glycerol, and glycerol esters including glycerol tripalmitate, glycerol distearate, glycerol tristearate, glycerol dimyristate, and glycerol trimyristate; longchain alcohols including n-decyl alcohol, lauryl alcohol, myristyl alcohol, cetyl alcohol, and n-octadecyl alcohol; 6-(5-cholesten-3.beta.-yloxy)-1-thio-.beta.-D-galactopyranoside; digalactosyldiglyceride; 6-(5-cholesten-3.beta.-yloxy)hexyl-6-amino-6-deoxy-1-thio-.beta.-D-galacto pyranoside; 6-(5-cholesten-3.beta.-yloxy)hexyl-6-amino-6-deoxyl-1-thio-.alpha.-D-manno pyranoside; 12-(((7'-diethylaminocoumarin-3-yl)carbonyl)methylamino)-octadecanoic acid; N-12-(((7'-diethylaminocoumarin-3-yl)carbonyl)methyl-amino) octadecanoyl-2-aminopalmitic acid; cholesteryl(4'-trimethylammonio)butanoate; N-succinyldioleoyl-phosphatidylethanolamine; 1,2-dioleoyl-sn-glycerol; 1,2-dipalmitoyl-sn-3-succinylglycerol; 1,3-dipalmitoyl-2-succinylglycerol; 1-hexadecyl-2-palmitoylglycerophosphoe thanolamine and palmitoylhomocysteine; and/or combinations thereof.

The present inventive essentially pH neutral vaginal drug delivery systems may further comprise an other excipient selected from the group consisting of lubricants, cleansing agents, deodorizers, humectants, emollients, plasticizers, binders, emulsifying agents, stabilizing agents, solvents, bioabsorbable materials, solubilizing agents, antimicrobial preservatives, diluents, glidants, suspending agents, extended-release agents, coating agents, adsorbents, disintegrants, chelating agents, and mixtures and combinations thereof.

Exemplary non-limiting lubricants which may be of use as other excipients according to the present inventive subject matter are selected from the group consisting of calcium stearate, canola oil, glyceryl palmitostearate, hydrogenated vegetable oil, magnesium oxide, mineral oil, poloxamer, polyethylene glycol, polyvinyl alcohol, sodium benzoate, sodium lauryl sulfate, sodium stearyl fumarate, stearic acid, sterilizable corn starch, talc, zinc stearate, and mixtures thereof.

Exemplary non-limiting humectants which may be of use as other excipients according to the present inventive subject matter are selected from the group consisting of glycerin, propylene glycol, sorbitol, triacetin, and mixtures thereof.

Exemplary non-limiting emollients which may be of use as other excipients according to the present inventive subject matter are selected from the group consisting of cetearyl, lanolin, mineral oil, petrolatum, cetyl esters wax, cholesterol, glycerol, glyceryl monostearate, isopropyl myristate, isopropyl palmitate, lecithin, and mixtures thereof.

Exemplary non-limiting plasticizers which may be of use as other excipients according to the present inventive subject matter are selected from the group consisting of lanolin, mineral oil, petrolatum, benzyl phenylformate, chlorobutanol, diethyl phthalate, glycerol, polyethylene glycol, sorbitol, triacetin, diethyl sebacate, triethyl citrate, cronotic acid, propylene glycol, butyl phthalate, dibtuyl sebacate, castor oil, and mixtures thereof. As is evident, the plasticizers may be hydrophobic as well as hydrophilic in nature.

Exemplary non-limiting binders which may be of use as other excipients according to the present inventive subject matter are selected from the group consisting of acacia, alginic acid, carboxymethylcellulose, hydroxyethylcellulose, hydroxypropylcellulose, dextrin, ethylcellulose, gelatin, liquid glucose, hydrogenated vegetable oil, hydroxypropylmethylcellulose, magnesium aluminum silicate, maltodextrin, methylcellulose, polyethylene oxide, polymethacrylates, povidone, sodium alginate, starch, zein, acrylic and methacrylic acid copolymers, pharmaceutical glaze, gums such as guar gum, and milk derivatives such as whey and starches, as well as other conventional binders well known to persons skilled in the art.

Exemplary non-limiting stabilizing agents which may be of use as other excipients according to the present inventive subject matter are selected from the group consisting of acacia, albumin, polyvinyl alcohols, alginic acid, bentonite, carboxymethylcellulose, hydroxypropyl cellulose, colloidal silicon dioxide, cyclodextrins, glyceryl monostearate, hydroxypropyl methylcellulose, magnesium aluminum silicate, propylene glycol, propylene glycol alginate, sodium alginate, wax, xanthan gum, and mixtures thereof.

Exemplary non-limiting solvents which may be of use as other excipients according to the present inventive subject matter are selected from the group consisting of alcohol, benzyl phenylformate, corn oil, cottonseed oil, diethyl phthalate, ethyl oleate, glycerol, glycofurol, isopropyl alcohol, isopropyl myristate, medium-chain triglycerides, mineral oil, peanut oil, polyethylene glycol, propylene carbonate, propylene glycol, sesame oil, soybean oil, triacetin, and mixtures thereof.

Exemplary non-limiting solubilizing agent which may be of use as other excipients according to the present inventive subject matter are selected from the group consisting of benzalkonium chloride, castor oil, cyclodextrins, polyoxyethylene ethers, glyceryl monostearate, lecithin, poloxamer, polysorbates, polyoxyethylene stearates, sorbitan esters, stearic acid, and mixtures thereof.

Exemplary non-limiting antimicrobial preservatives which may be of use as other excipients according to the present inventive subject matter are selected from the group consisting of benzoic acid, EDTA, phenolic acid, sorbic acid, benzyl alcohol, isopropyl alcohol, benzethonium chloride, bronopol, butylparaben, cetrimide, chlorhexidine, chlorobutanol, chlorocresol, cresol, ethylparaben, glycerol, imidurea, methylparaben, phenol, phenoxyethanol, phenylmercuric acetate, phenylmercuric borate, phenylmercuric nitrate, potassium sorbate, propylene glycol, propylparaben, sodium benzoate, sodim propionate, sorbic acid, thimerosol, and mixtures thereof.

Exemplary non-limiting diluents which may be of use as other excipients according to the present inventive subject matter are selected from the group consisting of calcium phosphate, calcium sulfate, carboxymethylcellulose calcium, cellulose, cellulose acetate, dextrates, dextrin, dextrose, fructose, glyceryl palmitostearate, kaolin, lactitol, lactose, magnesium carbonate, magnesium oxide, maltitol, maltodextrin, maltose, microcrystalline cellulose, polymethacrylates, powdered cellulose, pregelatinized starch, silicified microcrystalline cellulose, sodium chloride, sorbitol, starch, sucrose, sugar, talc, hydrogenated vegetable oil, and mixtures thereof.

Exemplary non-limiting glidants which may be of use as other excipients according to the present inventive subject matter are selected from the group consisting of maltitol, polydextrose, sucrose, and mixtures thereof.

Exemplary non-limiting suspending agents which may be of use as other excipients according to the present inventive subject matter are selected from the group consisting of alginic acid, bentonite, carbomer, carboxymethylcellulose, hydroxyethyl cellulose, hydroxypropyl cellulose, microcrystalline cellulose, dextrin, gelatin, guar gum, xanthan gum, kaolin, magnesium aluminum silicate, maltitol, methylcellulose, polysorbates, povidone, propylene glycol alginate, sodium alginate, sorbitan esters, tragacanth, and mixtures thereof.

Exemplary non-limiting extended-release agents which may be of use as other excipients according to the present inventive subject matter are selected from the group consisting of carrageenan, cellulose acetate, glyceryl monostearate, zein, and mixtures thereof.

Exemplary non-limiting disintegrants which may be of use as other excipients according to the present inventive subject matter are selected from the group consisting of alginic acid, carboxymethylcellulose, hydroxypropyl cellulose, microcrystalline cellulose, colloidal silicon dioxide, croscarmellose sodium, crospovidone, magnesium aluminum silicate, methylcellulose, polacrilin, povidone, sodium alginate, sodium starch glycolate, starch, and mixtures thereof.

Exemplary non-limiting chelating agents which may be of use as other excipients according to the present inventive subject matter are selected from the group consisting of EDTA, malic acid, maltol, and mixtures thereof.

It is an important feature of the present inventive subject matter that while the drug delivery system as a whole is essentially pH neutral, the internal water-soluble phase comprises an acidic buffered phase comprising a therapeutically active drug or drugs either alone or in combination with an additional buffering agent. The establishment of the acidic pH buffer within the internal phase has been shown to increase efficacy of antifungals and other antimicrobials that are incorporated therein. This increased efficacy is possibly a result of the buffer components diffusing to the vaginal lumen and buffering the pH of vaginal secretions to a pH of approximately 4.5. While a physiologically optimal pH for the vaginal vault, this pH is detrimental to common pathogens, such as *Candida* species within the fungal pathogens and *Enterococci* within the bacterial pathogens. Additionally, since a pH of 4.5, or thereabouts, is optimal for the vaginal environment, this pH will also aid in resolving irritation, itching, and other discomforts seen in acute infective disorders. As a result, the compositions of the presently claimed invention serve to optimize the cure of these pathogens.

Normally, administration of an acidic composition to the vaginal vault will irritate the vaginal lumen causing great discomfort. Accordingly, the present inventive subject matter is directed to an essentially pH neutral vaginal drug delivery system. Only the buffered internal phase of the globules making up this delivery system is acidic. The fully acidic buffered internal phase of the globules will not irritate the vaginal lumen since the buffer system is sequestered inside the globule walls. Therefore, the acidic buffer is not immediately in contact with the vaginal lining. If one were to try to take a pH reading on the emulsion, no reading would register until the delivery of the internal phase begins, resulting in an essentially pH neutral drug delivery system.

An additional advantage to the present essentially pH neutral drug delivery systems is that the acidic buffer components of the internal acidic buffered phase are released from the internal phase of the globules slowly, i.e. over a period of up to about 168 hours. This avoids a sudden acidic shock to the surrounding tissues. This is of particular importance within a highly irritated and infected vaginal cavity.

Accordingly, the internal acidic buffered phase of the globules is positively charged and has an internal pH of less than 6.0. In a preferred embodiment, the acidic buffered phase has an internal pH of between about 2.5 to about 5.5. In a particularly preferred embodiment, the acidic buffered phase has an internal pH of between about 3.5 to about 5.0.

Preferred buffer solutions useful in the acidic buffered phase are composed of a weak acid and a salt of the acid or a weak base and a salt of the base. Preferred non-limiting examples of buffer systems useful according to the presently claimed invention are selected from the group consisting of acetic acid/sodium or potassium acetate, ammonium chloride/ammonium hydroxide, benzoic acid/sodium or potassium benzoate, boric acid/sodium borate, citric acid/dibasic sodium phosphate, citric acid/sodium or potassium citrate, lactic acid/sodium or potassium lactate, mono and dibasic sodium or potassium phosphate, potassium hydrogen phthalate/hydrochloric acid, succinic acid/sodium or potassium succinate, and tartaric acid/sodium or potassium tartrate.

Additionally, the present inventive delivery systems provide for a release rate of the therapeutically active drug or drugs which is from about 0.1 hours to about 168 hours. In another preferred embodiment, the present inventive delivery systems provide for a release rate of the therapeutically active drug or drugs which is from about 0.1 hours to about 72 hours.

Another aspect of the present inventive subject matter affecting the release rate of the therapeutically active drug or drugs is the ability to adjust the osmotic pressure of the acidic buffered phase of the globules across a wide range of osmolarity. Accordingly, the acidic buffered phase of the globules can be isotonic, hypertonic, or hypotonic. The ability to produce globules of varying osmolarity is another advantage to the use of the present essentially pH neutral vaginal drug delivery systems.

In a preferred embodiment, the acidic buffered phase of the globules is isotonic. An isotonic acidic buffered phase will have the same osmotic pressure as biological tissue, equal to 300±10 milliosmol/liter. An isotonic acidic buffered phase releases the therapeutically active drug or drugs from the globule by diffusion. Accordingly, a globule having an isotonic acidic buffered phase can provide modified release of the therapeutically active drug or drugs for as long as multiple days or weeks after a single application.

In another preferred embodiment, the acidic buffered phase of the globules is hypertonic. A hypertonic acidic buffered phase will have a higher osmotic pressure than biological tissue, i.e. greater than 300±10 milliosmol/liter. A hypertonic acidic buffered phase releases the therapeutically active drug or drugs from the globule by rupture of the globule. Accordingly, the therapeutically active drug or drugs is delivered to the area of action within about 5 minutes to about 60 minutes after administration.

In yet another preferred embodiment, the acidic buffered phase of the globules is hypotonic. A hypotonic acidic buffered phase will have a lower osmotic pressure than biological tissue, i.e. less than 300±10 milliosmol/liter. A hypotonic acidic buffered phase releases the therapeutically active drug or drugs from the globule by diffusion and permeation. Accordingly, the therapeutically active drug or drugs is delivered to the area of action for about at least 1 hour after administration.

Accordingly, in one embodiment of the present inventive subject matter, the acidic buffered phase has an osmotic pressure greater than 300±10 milliosmol/liter. In yet another embodiment of the present inventive subject matter, the acidic buffered phase has an osmotic pressure less than 300±10 milliosmol/liter. In still another embodiment of the present inventive subject matter, the acidic buffered phase has an osmotic pressure equal to 300±10 milliosmol/liter.

Other factors which affect the release rate of the therapeutically active drug or drugs are the percentage of therapeutically active drug contained in each of the phases; thickness of the external membrane; amount and nature of emulsifier in the external phase or film; pH of the internal phase; diffusibility of the active species through the external phase or film membrane; etc. Within the physiological environment of the vaginal cavity, all of the chemical and physical forces present, including fluids, enzymes, pH, chemical balance, temperature, and shear forces from body movement affect the rate of breakdown of the system. These forces do not affect the integrity of the instant systems at the same rate as with known systems.

The therapeutically active drug or drugs useful according to the present inventive subject matter may be any of those which are approved for or used for the treatment, prophylaxis, cure, or mitigation of any disease of the vagina, urinary tract, cervix, or other female reproductive organ or inducement of conception; for aesthetic or cosmetic usage; for diagnostic purposes; for systemic drug therapy; or for sex determination of offspring. The agent must have utility when administered by delivery to all or a portion of the vaginal surfaces. Potential agents are normally well-known due to their need for governmental approval or common usage. The use of these therapeutically active drug or drugs in the compositions of the presently claimed invention serve to optimize the cure delivered by these agents.

A preferred therapeutically active drug or drugs useful in the presently claimed drug delivery systems is selected from the group consisting of antifungal agents, antibacterial agents, antimicrobial agents, antiviral agents, spermicides, hormone agents, antitrichomonial agents, antiprotozoan agents, antimycoplasm agents, antiretroviral agents, nucleoside analogues, reverse transcriptase inhibitors, protease inhibitors, contraceptive agents, sulfadrugs, sulfonamides, sulfones, hygiene agents, probiotic agents, vaccine agents, antibody agents, peptide agents, protein agents, polysaccharide agents, nucleic acids, plasmids, liposomes, carbohydrate polymers, transgenic bacteria, yeast, chemotherapeutic agents, steroid agents, growth enhancing agents, libido enhancers, androgenic substances, chitin derivatives, environment modifying agents such as pH modifiers, and mixtures and combinations thereof.

In a preferred embodiment, the therapeutically active drug is an antifungal agent. In a particularly preferred embodiment, the therapeutically active drug is an antifungal agent selected from the group consisting of butoconazole nitrate, clotrimazole, ketoconazole nitrate, miconizole, polyene antifungals, nystatin, amphotericin B, pimaricin, oxiconazole nitrate, terconazole nitrate, tioconazole, flutrimazole, intraconizole, allylamines, terbenafine, butenafine, amorolfine, naftifine, gluconazole, azoles, econazole, voriconizole, fluconazole, posaconazole, sulconazole, diction bis-benzimidazoles, glucan synthesis inhibitor, echinacandins, anidulafungin, caspofungin, micafugin, anti-tb drugs, diaphenylsulfone, ciclopirox olamine, haloprogin, tolnatane, undecylenate and mixtures and combinations thereof.

In another preferred embodiment, the therapeutically active drug is an antibacterial agent. In a particularly preferred embodiment, the therapeutically active drug is an antibacterial agent selected from the group consisting of clindamycin, sulfonamides, erythromycin, clarithromycin, azythromycin, tetracycline, doxacline, metronidazole, macrolides, ketolides, quinolones, cephalosporins, carbapenmens, penicillins, gentamicin, magainin peptides, dalbavancin, ramoplanin, iseganan, cefoxitin, ceftriaxone, trichloroacetic acid, and mixtures and combinations thereof.

In yet another preferred embodiment, the therapeutically active drug is an antiviral agent. In a particularly preferred embodiment, the therapeutically active drug is an antiviral agent selected from the group consisting of penciclovir, acylovir, ganciclovir, foscarnet, valaciclovir, pleconaril, and mixtures and combinations thereof.

In still another preferred embodiment, the therapeutically active drug is a spermicide. In a particularly preferred embodiment, the therapeutically active agent is the spermicide nonoxyl-9.

In another preferred embodiment, the therapeutically active drug is a growth enhancing agent. In a particularly preferred embodiment, the therapeutically active agent is a growth enhancing agent selected from the group consisting of cytokines.

In yet another preferred embodiment, the therapeutically active drug is a surface active drug. In a particularly preferred embodiment, the surface active drug is clindamycin phosphate.

In yet another preferred embodiment, the therapeutically active drug is an androgenic substance. In a particularly preferred embodiment, the androgenic substance is selected from the group consisting of danazol, testosterone, and mixtures and combinations thereof.

The therapeutically active drug or drugs in the internal water-soluble phase of the present drug delivery system is micronized and has a particle size ranging from about 0.1 microns to less than 60 microns. In a preferred embodiment, the therapeutically active drug or drugs has a particle size ranging from about 0.1 microns to about 15 microns. Accordingly, both soluble and less soluble drugs can be used in the present drug delivery systems.

One possible explanation for the increase in efficacy for therapeutically active drugs which are less soluble, such as butaconazole, clotrimazole, and flutrimazole, shown by the present delivery systems is believed to be related to the dissolution rate increase that is seen with a decreasing particle size of relatively water-insoluble drugs. It is believed that the micronized therapeutically active drug or drugs present in the internal water-soluble phase can rapidly adjust to changes in the equilibrium between the amount of therapeutically active drug contained outside of the internal phase and that which resides within the internal phase. A rapid dissolution allows a rapid re-establishment of this equilibrium. Without micronization, time must pass for equilibrium to be re-established, resulting in lower amounts of diffusable therapeutically active drug or drugs at the site of infection.

In another embodiment of the present inventive subject matter, the external water-insoluble phase or film contains an additional therapeutically active drug outside of the acidic buffered phase. In a preferred embodiment, the additional therapeutically active drug in the external phase or film is micronized and has a particle size ranging from about 0.5 microns to less than 60.0 microns. In another preferred embodiment, the additional therapeutically active drug in the external phase or film is non-micronized. In yet another preferred embodiment, the additional therapeutically active drug in the external phase or film is both micronized and non-micronized.

In a preferred embodiment of the present inventive subject matter, the ratio of the micronized drug in the acid buffered phase and the micronized drug outside of the acid buffered phase to the nonmicronized drug is about 0.1 to about 1,000.

The present drug delivery systems can be administered into the vaginal cavity by the use of conventional applicators or other coating, spraying, foaming, or aerosol means or any other available means known to a person of ordinary skill in the art of pharmaceutical administration technology.

Although the systems are deformable at physiological temperatures, approximately 37° C., they do not lose their integrity as do the systems of the prior art. These delivery systems, unlike presently known systems, are not characterized by leakage from the vaginal cavity following the insertion of the system. Since these systems break down over an extended period, their nonaqueous components are either absorbed or released from the vaginal cavity at a rate which is less than with conventional formulations.

Exemplary delivery systems useful according to the presently claimed subject matter include but are not limited to dispersions, solids, suspensions, ointments, cataplasms (poultices), pastes, powders, ovules, suppositories, foams, dressings, creams, solutions, liquids, jelly, sprays, gels, tablets (including quick-dissolving tablets), tampons, sponges, pillows, puffs, and patches.

The present inventive subject matter also contemplates methods for treating a vaginal disorder comprising administering to a patient the essentially pH neutral vaginal drug delivery systems described herein. In particular, the vaginal disorder is selected from the group consisting of infection caused by a *Candida* species, *Enterococci* species, *Streptococci* species, *Staphylococci* species, uropathogens, *E. coli, Kelbsiella, Clostridia* species, *Mobiluncus* species, *Gardnerella, Prevotella* species, bacteria pseudomonas, protozoans, mycoplasm, *Chlamydia*, HIV, HPV, herpes, nonspecific vaginitis, *N. gonorrhoeae, Trichomonas vaginalis, C. trachomatis*, and mixtures and combinations thereof.

Additional vaginal disorders which may be treated according to the present inventive subject matter include all forms of endometriosis, exterior endometriosis, endometritis, cancer, ovarian cysts, salpingitis, uterine fibroids, other genital viral diseases, genital warts, and mixtures and combinations thereof.

The globules of the presently claimed invention can be made by a variety of devices which provide sufficiently high shear for shear mixing. There are a large variety of these devices available on the market including a microfluidizer such as is made by Biotechnology Development Corporation, a "French"-type press, or some other device which provides a high enough shear force.

A device which is particularly useful for making the globules of the present invention has been developed by Micro Vesicular Systems, Inc., Vineland, N.J., and is further described in U.S. Pat. No. 4,895,452, hereby incorporated by reference in its entirety.

This device has a substantially cylindrical mixing chamber with at least one tangentially located inlet orifice. One or more orifices lead to a reservoir for the water-insoluble phase and at least one of the other orifices is attached to a reservoir for the water-soluble phase.

The different phases are driven into the cylindrical chamber through pumps, e.g. positive displacement pumps, and intersect in such a manner as to form a turbulent flow within the chamber. The globules are removed from the chamber through an axially located discharge orifice.

In the water-soluble phase chamber a biologically active therapeutic is mixed with the diluent. In the water-insoluble chamber the stabilizing compounds are added. Both phases are then mixed in the cylindrical chamber at about 30,000 revolutions per minute ("rpm") while surfactants are added to the cylindrical chamber.

Several non-limiting examples of surfactants useful according to the presently claimed invention include docusate sodium, sodium lauryl sulfate, cetrimide, polyoxyethylene fatty acid esters, and sorbitan esters.

One of ordinary skill in the art without undue experimentation could vary the rpm of the high shear homogenization to produce substantially the same invention without deviating from the disclosure presented herein. Moreover, methods for the preparation of such pH neutral vaginal drug delivery systems will be readily apparent to those skilled in the art, in view of the present disclosure, when the present disclosure is coupled with information known in the art.

Theory of the Invention

Without limiting the theory of the invention to any particular theory, several possible explanations arise for the novel mechanisms of the emulsions having globules provided herein.

Under a Pulsed Emulsion Phenomenon Theory ("PEP"), the release of the therapeutically active drug or drugs from the acidic buffered phase of the globules is dependent on either the environmental pH or the type of ambient enzymes present. Under a pH-dependent model, the globules dock to the vaginal mucosal lining and release the biologically active therapeutic when at a proper ambient pH.

Under an enzyme-dependent model, a biologically present enzyme could either trigger or prevent the docking/release event. For example, lipase present in the vaginal cavity could trigger a docking/release event releasing the therapeutic into the vaginal cavity for absorption through the mucosal membrane.

A Mucosal Docked Vesicle Theory posits that significant absorption only occurs at a mucosal epithelium. It is possible that the globules only interact with the mucosal basal membrane or with the mucous itself. Docking/releasing events only seem to occur at mucosal surfaces. Upon a docking/releasing event, biologically active drugs sequestered in the vesicle diffuse across the mucosal basal membrane and enter the bloodstream for distribution.

Another explanation for the docking/release event are VanderWaal interactions occurring between the globules and the mucosal membrane. VanderWaal forces are temporary dipoles induced in one molecule by another molecule. This physical interaction would be similar to the "static cling" of plastic decals to glass used in place of adhesive decals for auto windows. VanderWaal forces may trigger docking and subsequent release.

One of ordinary skill in the art will understand that the particular theory of the invention is not limited to any single one of the above theories, or may be a combination of the above theories or involve theories as of yet not ascertainable and do not limit in any way to the ability to practice the invention as disclosed herein.

The following examples are illustrative of preferred embodiments of the invention and are not to be construed as limiting the invention thereto. All polymer molecular weights are mean average molecular weights. All percentages are based on the percent by weight of the final delivery system or formulation prepared unless otherwise indicated and all totals equal 100% by weight.

EXAMPLES

Metronidazole and clindamycin exemplify the problems confronted in the art in designing an effective vaginal drug delivery system. The medicinal properties of metronidazole and clindamycin can be readily altered using any number of techniques, but their physiochemical properties have limited the design of viable delivery systems.

The essentially pH neutral vaginal drug delivery system of the presently claimed invention was used to prepare the following example.

Example I

TABLE I

| Ingredient | Amount % w/w |
| --- | --- |
| Purified water | 24.676 |
| Glycerin | 47.250 |
| Glacial acetic acid | 0.225 |
| Sodium acetate | 0.200 |
| Sodium chloride | 0.750 |
| Methylparaben | 0.090 |
| Propylparaben | 0.035 |
| Butylparaben | 0.024 |
| Sucrose | 8.000 |
| Metronidazole | 0.750 |
| Mineral oil | 13.000 |
| Polyethylene Glycol (30) Dipolyhydroxystearate | 5.000 |

The globules used in the present drug delivery systems can be made by a variety of devices known in the art which provides sufficiently high shear for shear mixing. A device which is particularly useful has been developed by Micro Vesicular Systems, Inc., Vineland, N.J. and is further described in U.S. Pat. No. 4,895,452. The temperature utilized is dependent upon the end product desired. The pH of the internal water-soluble phase of the globules is measured prior to the manufacture of the globules to ensure that the pH is within the critical pH range set forth herein.

The formulas described in these examples were produced by the following method:

The metronidazole and additional components of the internal water-soluble phase are mixed with the purified water. The ingredients of the external water-insoluble phase or film are mixed together in a second vessel. The internal water-soluble phase is slowly added to the external water-insoluble phase or film while the two phases are mixed together with a split-disk stirrer until addition is complete and the desired viscosity is obtained. Mixing speed is dependent on the final end product desired.

Example II

The method of Example I may be used to produce a clindamycin phosphate delivery system according to the following formula:

TABLE II

| Ingredient | Amount % w/w |
|---|---|
| Purified water | 24.676 |
| Glycerin | 45.200 |
| Glacial acetic acid | 0.225 |
| Sodium acetate | 0.200 |
| Sodium chloride | 0.750 |
| Methylparaben | 0.090 |
| Propylparaben | 0.035 |
| Butylparaben | 0.024 |
| Sucrose | 8.000 |
| Clindamycin Phosphate | 2.800 |
| Mineral oil | 12.000 |
| Polyethylene Glycol (30) Dipolyhydroxystearate | 6.000 |

The invention being thus described, it will be obvious that the same may be varied in many ways. Such variations are not to be regarded as a departure from the spirit scope of the invention and all such modifications are intended to be included within the scope of the following claims.

We claim:

1. An essentially pH neutral vaginal drug delivery system, which comprises:
    an essentially pH neutral emulsion having globules having two phases, an internal water-soluble phase and an external water-insoluble phase or film;
    said internal water-soluble phase comprises an acidic buffered phase containing a therapeutically active drug or drugs, wherein the acidic buffered phase comprises said therapeutically active drug or drugs either alone or in combination with an additional buffering agent;
    wherein the acidic buffered phase is isotonic, hypertonic, or hypotonic; and
    wherein the globules have a particle size ranging from about 0.1 microns to about 100 microns.

2. The composition of claim 1, wherein the therapeutically active drug or drugs is micronized and has a particle size ranging from about 0.1 microns to less than 60 microns.

3. The composition of claim 2, wherein the therapeutically active drug or drugs has a particle size ranging from about 0.1 microns to about 15 microns.

4. The composition of claim 1, wherein the globules have a particle size ranging from about 0.1 microns to about 60 microns.

5. The composition of claim 4, wherein the globules have a particle size ranging from about 0.5 microns to about 55 microns.

6. The composition of claim 1, wherein the acidic buffered phase has an internal pH of less than 6.0.

7. The composition of claim 6, wherein the acidic buffered phase has an internal pH of between about 2.5 to about 5.5.

8. The composition of claim 7, wherein the acidic buffered phase has an internal pH of between about 3.5 to about 5.0.

9. The composition of claim 1, wherein the therapeutically active drug is selected from the group consisting of antifungal agents, antibacterial agents, antimicrobial agents, antiviral agents, spermicides, hormone agents, antitrichomonial agents, antiprotozoan agents, antimycoplasm agents, antiretroviral agents, nucleoside analogues, reverse transcriptase inhibitors, protease inhibitors, contraceptive agents, sulfadrugs, sulfonamides, sulfones, hygiene agents, probiotic agents, vaccine agents, antibody agents, peptide agents, protein agents, polysaccharide agents, nucleic acids, plasmids, liposomes, carbohydrate polymers, transgenic bacteria, yeast, chemotherapeutic agents, steroid agents, growth enhancing agents, libido enhancers, androgenic substances, chitin derivatives, environment modifying agents, pH modifiers, and mixtures and combinations thereof.

10. The composition of claim 9, wherein the therapeutically active drug is a growth enhancing agent selected from the group consisting of cytokines.

11. The composition of claim 1, further comprising an excipient selected from the group consisting of lubricants, cleansing agents, deodorizers, humectants, emollients, plasticizers, binders, emulsifying agents, stabilizing agents, solvents, bioabsorbable materials, antioxidants, solubilizing agents, antimicrobial preservatives, diluents, glidants, suspending agents, extended-release agents, coating agents, adsorbents, disintegrants, chelating agents, and mixtures and combinations thereof.

12. The composition of claim 9, wherein the therapeutically active drug is an antifungal agent selected from the group consisting of butoconazole nitrate, clotrimazole, ketoconazole nitrate, miconizole, polyene antifungals, nystatin, amphotericin B, pimaricin, oxiconazole nitrate, terconazole nitrate, tioconazole, flutrimazole, intraconizole, allylamines, terbenafine, butenafine, amorolfine, naftifine, gluconazole, azoles, econazole, voriconizole, fluconazole, posaconazole, sulconazole, diction bis-benzimidazoles, glucan synthesis inhibitor, echinacandins, anidulafungin, caspofungin, micafugin, anti-tb drugs, diaphenylsulfone, ciclopirox olamine, haloprogin, tolnatane, undecylenate, and mixtures and combinations thereof.

13. The composition of claim 9, wherein the therapeutically active drug is an antibacterial agent selected from the group consisting of clindamycin, sulfonamides, erythromycin, clarithromycin, azythromycin, tetracycline, doxacline, metronidazole, macrolides, ketolides, quinolones, cephalosporins, carbapenmens, penicillins, gentamicin, magainin peptides, dalbavancin, ramoplanin, iseganan, cefoxitin, ceftriaxone, trichloroacetic acid, and mixtures and combinations thereof.

14. The composition of claim 9, wherein the therapeutically active drug is an antiviral agent selected from the group consisting of penciclovir, acylovir, ganciclovir, foscarnet, valaciclovir, pleconaril, and mixtures and combinations thereof.

15. The composition of claim 9, wherein the therapeutically active drug is the spermicide nonoxyl-9.

16. The composition of claim 9, wherein the androgenic substances are selected from the group consisting of danazol, testosterone, and mixtures and combinations thereof.

17. The composition of claim 1, wherein the external water-insoluble phase or film contains an additional therapeutically active drug outside of the acidic buffered phase.

18. The composition of claim 17, wherein the additional therapeutically active drug in the external phase or film is micronized and has a particle size ranging from about 0.5 microns to less than 60.0 microns.

19. The composition of claim 17, wherein the additional therapeutically active drug in the external phase or film is non-micronized.

20. The composition of claim 17, wherein the additional therapeutically active drug in the external phase or film is both micronized and non-micronized.

21. The composition of claim 20, wherein the ratio of the micronized drug in the acid buffered phase and the micronized drug outside of the acid buffered phase to the nonmicronized drug is about 0.1 to about 1,000; and wherein the release rate of the therapeutically active drug is from about 0.1 hours to about 168 hours.

22. The composition of claim 1, wherein the acidic buffered phase has an osmotic pressure greater than 300±10 milliosmol/liter.

23. The composition of claim 1, wherein the acidic buffered phase has an osmotic pressure less than 300±10 milliosmol/liter.

24. The composition of claim 1, wherein the acidic buffered phase has an osmotic pressure equal to 300±10 milliosmol/liter.

25. The composition of claim 1, wherein the therapeutically active drug is a surface active drug.

26. The composition of claim 25, wherein the surface active drug is clindamycin phosphate.

27. An essentially pH neutral vaginal drug delivery system, which comprises:
   an essentially pH neutral emulsion having globules having two phases, an internal water-soluble phase and an external water-insoluble phase or film;
   said internal water-soluble phase comprises an acidic buffered phase containing a micronized therapeutically active drug or drugs, wherein the acidic buffered phase comprises said micronized therapeutically active drug or drugs either alone or in combination with an additional buffering agent;
   wherein the acidic buffered phase is isotonic, hypertonic, or hypotonic; and
   wherein the micronized therapeutically active drug has a particle size ranging from about 0.1 microns to less than 60.0 microns;
   wherein the efficacy of the therapeutically active drug is maximized by the acidic buffered phase; and
   wherein the acidic buffered phase is present in an amount sufficient to provide a cessation of symptoms of irritation and itching of the vaginal mucosa.

28. The composition of claim 27, wherein the acidic buffered phase is positively charged and has an internal pH of between about 2.5 to about 5.0.

29. The composition of claim 27, wherein the therapeutically active drug is selected from the group consisting of antifungal agents, antibacterial agents, antimicrobial agents, antiviral agents, spermicides, hormone agents, antitrichomonial agents, antiprotozoan agents, antimycoplasm agents, antiretroviral agents, nucleoside analogues, reverse transcriptase inhibitors, protease inhibitors, contraceptive agents, sulfadrugs, sulfonamides, sulfones, hygiene agents, probiotic agents, vaccine agents, antibody agents, peptide agents, protein agents, polysaccharide agents, nucleic acids, plasmids, liposomes, carbohydrate polymers, transgenic bacteria, yeast, chemotherapeutic agents, steroid agents, growth enhancing agents, libido enhancers, androgenic substances, chitin derivatives, environment modifying agents, pH modifiers, and mixtures and combinations thereof.

30. The composition of claim 29, wherein the therapeutically active drug is a growth enhancing agent selected from the group consisting of cytokines.

31. The composition of claim 27, further comprising an excipient selected from the group consisting of lubricants, cleansing agents, deodorizers, humectants, emollients, plasticizers, binders, emulsifying agents, stabilizing agents, solvents, bioabsorbable materials, antioxidants, solubilizing agents, antimicrobial preservatives, diluents, glidants, suspending agents, extended-release agents, coating agents, adsorbents, disintegrants, chelating agents, and mixtures and combinations thereof.

32. The composition of claim 29, wherein the therapeutically active drug is an antifungal agent selected from the group consisting of butoconazole nitrate, clotrimazole, ketoconazole nitrate, miconizole, polyene antifungals, nystatin, amphotericin B, pimaricin, oxiconazole nitrate, terconazole nitrate, tioconazole, flutrimazole, intraconizole, allylamines, terbenafine, butenafine, amorolfine, naftifine, gluconazole, azoles, econazole, voriconizole, fluconazole, posaconazole, sulconazole, diction bis-benzimidazoles, glucan synthesis inhibitor, echinacandins, anidulafungin, caspofungin, micafugin, anti-tb drugs, diaphenylsulfone, ciclopirox olamine, haloprogin, tolnatane, undecylenate, and mixtures and combinations thereof.

33. The composition of claim 29, wherein the therapeutically active drug is an antibacterial agent selected from the group consisting of clindamycin, sulfonamides, erythromycin, clarithromycin, azythromycin, tetracycline, doxacline, metronidazole, macrolides, ketolides, quinolones, cephalosporins, carbapenmens, penicillins, gentamicin, magainin peptides, dalbavancin, ramoplanin, iseganan, cefoxitin, ceftriaxone, trichloroacetic acid, and mixtures and combinations thereof.

34. The composition of claim 29, wherein the therapeutically active drug is an antiviral agent selected from the group consisting of penciclovir, acylovir, ganciclovir, foscarnet, valaciclovir, pleconaril, and mixtures and combinations thereof.

35. The composition of claim 29, wherein the therapeutically active drug is the spermicide nonoxyl-9.

36. The composition of claim 29, wherein the androgenic substance is selected from the group consisting of danazol, testosterone, and mixtures and combinations thereof.

37. The composition of claim 27, wherein the external water-insoluble phase or film contains an additional therapeutically active drug outside of the acidic buffered phase.

38. The composition of claim 37, wherein the additional therapeutically active drug in the external phase or film is micronized and has a particle size ranging from about 0.5 microns to less than 60.0 microns.

39. The composition of claim 37, wherein the additional therapeutically active drug in the external phase or film is non-micronized.

40. The composition of claim 37, wherein the additional therapeutically active drug in the external phase or film is both micronized and non-micronized.

41. The composition of claim 40, wherein the ratio of the micronized drug in the acid buffered phase and the micronized drug outside of the acid buffered phase to the nonmicronized drug is about 0.1 to about 1,000; and wherein the release rate of the therapeutically active drug is from about 0.1 hours to about 72 hours.

42. The composition of claim 27, wherein the acidic buffered phase has an osmotic pressure greater than 300±10 milliosmol/liter.

43. The composition of claim 27, wherein the acidic buffered phase has an osmotic pressure less than 300±10 milliosmol/liter.

44. The composition of claim 27, wherein the acidic buffered phase has an osmotic pressure equal to 300±10 milliosmol/liter.

45. The composition of claim 27, wherein the therapeutically active drug is a surface active drug.

46. The composition of claim 45, wherein the surface active drug is clindamycin phosphate.

47. An essentially pH neutral vaginal drug delivery system, which comprises:

an essentially pH neutral emulsion having globules having two phases, an internal water-soluble phase and an external water-insoluble phase or film;

said internal water-soluble phase comprises an acidic buffered phase having an internal pH of about 2.0 to about 6.0 and a therapeutically active drug or drugs, wherein the acidic buffered phase comprises said therapeutically active drug or drugs either alone or in combination with an additional buffering agent; and wherein the globules have a particle size ranging from about 0.1 microns to about 100 microns.

48. The composition of claim 47, wherein the acidic buffered phase has an internal pH of between about 2.5 to about 5.5.

49. Method for treating a vaginal disorder comprising: administering to a patient an essentially pH neutral vaginal drug delivery system, which comprises:

an essentially pH neutral emulsion having globules having two phases, an internal water-soluble phase and an external water-insoluble phase or film;

said internal water-soluble phase comprises an acidic buffered phase containing a therapeutically active drug or drugs, wherein the acidic buffered phase comprises said therapeutically active drug or drugs either alone or in combination with an additional buffering agent;

wherein the acidic buffered phase is isotonic, hypertonic, or hypotonic; and wherein the therapeutically active drug has a particle size ranging from about 0.1 microns to less than 60.0 microns.

50. The method of claim 49, wherein the vaginal disorder is selected from the group consisting of infection caused by a *Candida* species, *Enterococci* species, *Streptococci* species, *Staphylococci* species, uropathogens, *E. coli, Kelbsiella, Clostridia* species, *Mobiluncus* species, *Gardnerella, Prevotella* species, bacteria pseudomonas, protozoans, mycoplasm, *Chlamydia*, HIV, HPV, herpes, *N. gonorrhoeae, Trichomonas vaginalis, C. trachomatis*, and mixtures and combinations thereof.

51. The method of claim 49, wherein the isotonic acidic buffered phase releases the therapeutically active drug or drugs from the globule by diffusion.

52. The method of claim 49, wherein the therapeutically active drug is delivered to the area of action within about 0.1 hour to about 168 hours after administration.

53. The method of claim 49, wherein the hypertonic acidic buffered phase releases the therapeutically active drug or drugs from the globule by rupture of the globule.

54. The method of claim 53, wherein the therapeutically active drug is delivered to the area of action within about 5 minutes to about 60 minutes after administration.

55. The method of claim 49, wherein the hypotonic acidic buffered phase releases the therapeutically active drug or drugs from the globule by diffusion and permeation.

56. The method of claim 55, wherein the therapeutically active drug is delivered to the area of action for about at least 1 hour after administration.

57. The method of claim 49, wherein the vaginal disorder is nonspecific vaginitis.

* * * * *